April 2, 1946. W. L. ROBERTS Plant Pat. 674
APRICOT TREE
Filed June 13, 1944
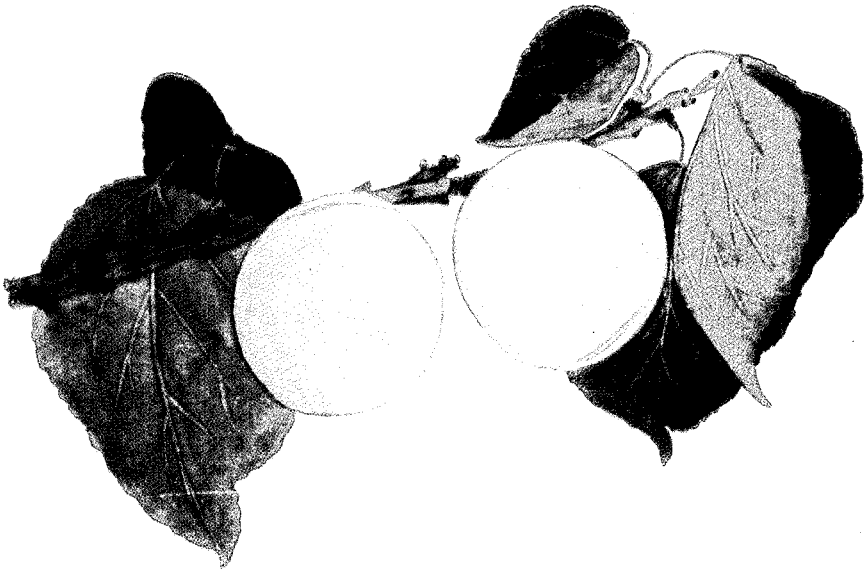
Inventor:
W. L. Roberts
By: Robb & Robb
attorneys.

Patented Apr. 2, 1946

Plant Pat. 674

UNITED STATES PATENT OFFICE

674

APRICOT TREE

William L. Roberts, Grandview, Wash., assignor to Stark Bro's Nurseries and Orchards Company, Louisiana, Mo., a corporation of Missouri Application June 13, 1944, Serial No. 540,063

1 Claim. (Cl. 47—62)

The present discovery appertains to a new and distinct variety of apricot tree originating as a chance seedling.

This new seedling discovered by me on property then owned by me in Yakima County, Washington, was characterized as to novelty primarily by its very early ripening habit—earlier in fact than any other variety now on the market of which I am aware. By way of comparison, this new variety is commercially ripe from one to two weeks ahead of the well known "Alexander" variety grown under comparable conditions, and since this last-named variety is one of the earliest commercial varieties now on the market, the value of the present apricot commercially, can well be understood.

In addition to the above-mentioned characteristic, this new apricot shows a bright red blush and orange ground color at the early ripening season, thus making it a very attractive early apricot.

Asexual reproduction of the new variety discloses that these important characteristics are established or fixed.

The drawing illustrates a twig with leaves and fruit, of this variety.

Other novel combinative features appear in the following detail description, in which color terminology accords with the general dictionary significance of the terms employed.

Dates first and last picking: June 17 and July 5.

Tree: Large; vigorous; dense; upright; hardy; very productive.

*Trunk.*—Medium stocky; medium smooth.

*Branches.*—Reddish Brown; dull. *Lenticels*—medium large; few.

*Leaves.*—Length—3¾ to 4¼″. Width—3½ to 4½″. Large; ovate; abruptly pointed; thick; Dark Green; smooth. Margin—crenate; finely serrate. Petiole—Medium length; medium thick. Glands—Average number—Two. Alternate; small; globose.

*Flowers.*—Dates first and full blossoms along with majority of other apricots. Medium early; large; Pink.

Fruit: Maturity when described—June 20th.

*Size.*—Medium. Axial diameter, 1¾″; transverse in suture plane, 1¾″; at right angles to suture plane, 1″.

*Form.*—Uniform; oblong; compressed laterally.

*Suture.*—Shallow.

*Base.*—*Rounded.*

*Apex.*—Rounded to truncate.

*Skin.*—Medium tough. Color—highly blushed red; down scant.

*Flesh.*—Orange - Yellow. Juice — abundant. Texture—firm. Fibres—tender. Ripens—fairly even. Flavor—subacid, mild. Aroma—wanting. Eating quality—best.

*Stone.*—Free. Size—medium large; length, 0.8 inch; thickness, 0.45 inch; width, 0.65 inch. Form—elliptical; bluntly pointed. Base—straight; narrow; oblong. Apex—acuminate. Sides—equal. Surface—furrowed near base and ventral edge. Ridges—rounded.

Use: Market; local; dessert.

Keeping quality: Medium.

Shipping quality: Good to medium.

The present variety is definitely distinct from the Yakimine and Riland varieties in important respects. Speaking with reference to the flesh, the new variety is a deep orange color extending all the way to the seed, while the Yakimine is a white-fleshed variety overspread with red, and the Riland is a greenish yellow with very little blush, these characteristics being observed as to specimens grown under comparable conditions.

In respect to the ripening period, this new apricot ripens from nine to twelve days earlier than either of the Yakimine or Riland varieties.

The foliage of the new variety differs from Yakimine and Riland in size, shape and other details; that is to say, the leaves are larger and longer than those of the latter two varieties, the petals being stouter and longer, and the glands being reniform and round with depressed center.

I claim:

A new and distinct variety of apricot tree, characterized as to novelty by the very early ripening period of its fruit, coloring of the fruit at the early season, and size and shape of the foliage, substantially as shown and described.

WILLIAM L. ROBERTS.